(12) United States Patent
Urabe et al.

(10) Patent No.: US 8,163,543 B2
(45) Date of Patent: Apr. 24, 2012

(54) AAV VECTORS PRODUCED IN INSECT CELLS

(75) Inventors: Masashi Urabe, Tochigi (JP); Keiya Ozawa, Tochigi (JP); Saskia Jacoba Petronella Haast, Huizen (NL); Wilhelmus Theodorus Johannes Maria Christiaan Hermens, Almere (NL)

(73) Assignee: Amsterdam Molecular Therapeutics B.V., Amsterdam (NL)

( * ) Notice: Subject to any disclaimer, the term of this patent is extended or adjusted under 35 U.S.C. 154(b) by 842 days.

(21) Appl. No.: 12/091,022

(22) PCT Filed: Oct. 19, 2006

(86) PCT No.: PCT/NL2006/050262
§ 371 (c)(1),
(2), (4) Date: Apr. 21, 2008

(87) PCT Pub. No.: WO2007/046703
PCT Pub. Date: Apr. 26, 2007

(65) Prior Publication Data
US 2012/0028357 A1 Feb. 2, 2012

(30) Foreign Application Priority Data
Oct. 20, 2005 (WO) ................ PCT/NL2005/050018

(51) Int. Cl.
*C12N 15/33* (2006.01)
*C12N 15/07* (2006.01)
*C12N 7/01* (2006.01)
(52) U.S. Cl. .................... 435/320.1; 435/348; 435/235.1
(58) Field of Classification Search .................. None
See application file for complete search history.

(56) References Cited

U.S. PATENT DOCUMENTS
2009/0191588 A1 * 7/2009 Hermens et al. ............. 435/69.1

FOREIGN PATENT DOCUMENTS
WO 03/042361 A 5/2003
WO 2004/099423 A1 11/2004

OTHER PUBLICATIONS

Urabe M et al: "Insect cells as a factory to produce adeno-associated virus type 2 vectors" Human Gene Therapy, Mary Ann Liebert, New York, NY, US, vol. 13, No. 16 Nov. 1, 2002, pp. 1935-1943 XP002394454.
Kohkbrenner et al: "Successful Production of Pseudotyped rAAV Vectors Using a Modified Baculovirus Expression System" Molecular Therapy, Academic Press, San Diego, CA, US, vol. 12, No. 6, Dec. 2005, pp. 1217-1225, XP005176630.
Urabe Masashi et al: "Scalable generation of high-titer recombinant adeno-associated virus type 5 in insect cells" Journal of Virology, vol. 80, No. 4, Feb. 2006, pp. 1874-1885, XP002429140.
Mehdi, H. et al., Gene 91:173-178 (1990).
Summerford, C. et al., Nature Medicine 5:587-588 (May 1999).
Verheesen, P. et al., Biochimica et Biophysica Acta 1624:21-28 (2003).

* cited by examiner

*Primary Examiner* — Michael Burkhart
(74) *Attorney, Agent, or Firm* — Browdy and Neimark PLLC

(57) ABSTRACT

The present invention relates to the production of adeno-associated viral vectors in insect cells. The insect cells therefore comprise a first nucleotide sequence encoding the adeno-associated virus (AAV) capsid proteins, whereby the initiation codon for translation of the AAV VP1 capsid protein is a non-ATG, suboptimal initiation codon. The insect cell further comprises a second nucleotide sequence comprising at least one AAV inverted terminal repeat (ITR) nucleotide sequence; a third nucleotide sequence comprising a Rep52 or a Rep40 coding sequence operably linked to expression control sequences for expression in an insect cell; and, a fourth nucleotide sequence comprising a Rep78 or a Rep68 coding sequence operably linked to expression control sequences for expression in an insect cell. The invention further relates to adeno-associated viral vectors with an altered ratio of the viral capsid proteins that provides improved infectivity of the viral particles.

21 Claims, 4 Drawing Sheets

SEQUENCE LISTING

<160> NUMBER OF SEQ ID NOS: 10

<210> SEQ ID NO 1
<211> LENGTH: 49
<212> TYPE: DNA
<213> ORGANISM: Artificial Sequence
<220> FEATURE:

-continued

<223> OTHER INFORMATION: primer

<400> SEQUENCE: 1
cgcggatcct gttaagacgg ctgccgacgg ttatctaccc gattggctc          49

<210> SEQ ID NO 2
<211> LENGTH: 49
<212> TYPE: DNA
<213> ORGANISM: Artificial Sequence
<220> FEATURE:
<223> OTHER INFORMATION: primer

<400> SEQUENCE: 2
cgcggatcct gttaagttgg ctgccgacgg ttatctaccc gattggctc          49

<210> SEQ ID NO 3
<211> LENGTH: 49
<212> TYPE: DNA
<213> ORGANISM: Artificial Sequence
<220> FEATURE:
<223> OTHER INFORMATION: primer

<400> SEQUENCE: 3
cgcggatcct gttaagattg ctgccgacgg ttatctaccc gattggctc          49

<210> SEQ ID NO 4
<211> LENGTH: 49
<212> TYPE: DNA
<213> ORGANISM: Artificial Sequence
<220> FEATURE:
<223> OTHER INFORMATION: primer

<400> SEQUENCE: 4
cgcggatcct gttaaggtgg ctgccgacgg ttatctaccc gattggctc          49

<210> SEQ ID NO 5
<211> LENGTH: 49
<212> TYPE: DNA
<213> ORGANISM: Artificial Sequence
<220> FEATURE:
<223> OTHER INFORMATION: primer

<400> SEQUENCE: 5
cgcggatcct gttaagctgg ctgccgacgg ttatctaccc gattggctc          49

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
gtcgtaggcc ttgtcgtgct cgagggccgc                              30

<210> SEQ ID NO 7
<211> LENGTH: 9
<212> TYPE: DNA
<213> ORGANISM: adeno-associated virus 2

<400> SEQUENCE: 7 cctgttaag                                                      9

<210> SEQ ID NO 8
<211> LENGTH: 10
<212> TYPE: DNA

```
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4)..(4)
<223> OTHER INFORMATION: r = purine = A or G
<220> FEATURE:
<221> NAME/KEY: misc_feature
<222> LOCATION: (7)..(9)
<223> OTHER INFORMATION: nnn is the sequence of suboptimal initiation
      codon ACT or ACG

<400> SEQUENCE: 8 gccrccnnng                                                           10

<210> SEQ ID NO 9
<211> LENGTH: 47
<212> TYPE: DNA
<213> ORGANISM: Artificial Sequence
<220> FEATURE:
<223> OTHER INFORMATION: forward primer

<400> SEQUENCE: 9
ccatcgggcg cggatcctgg ccgccacggc tgccgacggt tatctac                  47

<210> SEQ ID NO 10
<211> LENGTH: 46
<212> TYPE: DNA
<213> ORGANISM: Artificial Sequence
<220> FEATURE:
<223> OTHER INFORMATION: forward primer

<400> SEQUENCE: 10
ccatcgggcg cggatcctgc cgccctggct gccgacggtt atctac                   46
```

AAV VECTORS PRODUCED IN INSECT CELLS

FIELD OF THE INVENTION

The present invention relates to the production of adeno-associated virus in insect cells and to adeno-associated virus with an altered ratio of the viral capsid proteins that provides improved infectivity.

BACKGROUND OF THE INVENTION

Adeno-associated virus (AAV) may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) is being evaluated in gene therapy clinical trials for hemophilia B, malignant melanoma, cystic fibrosis, and other diseases.

Host cells that sustain AAV replication in vitro are all derived from mammalian cell types. Therefore, rAAV for use in gene therapy has thus far mainly been produced on mammalian cell lines such as e.g. 293 cells, COS cells, HeLa cells, KB cells, and other mammalian cell lines (see e.g. U.S. Pat. No. 6,156,303, U.S. Pat. No. 5,387,484, U.S. Pat. No. 5,741,683, U.S. Pat. No. 5,691,176, U.S. Pat. No. 5,688,676, US 20020081721, WO 00/47757, WO 00/24916, and WO 96/17947). rAAV vectors are typically produced in such mammalian cell culture systems by providing DNA plasmids that contain the therapeutic gene flanked by the origin of AAV replication (inverted terminal repeats or ITRs), genes for AAV replication proteins Rep78, Rep68, Rep52, and Rep40, and genes for virion or structural proteins VP1, VP2, and VP3. In addition, a plasmid containing early genes from adenovirus (E2A, E4ORF6, VARNA) is provided to enhance the expression of the AAV genes and improve vector yield (see e.g. Grimm et al., 1998, Hum. Gene Ther. 9: 2745-2760). However, in most of these mammalian cell culture systems, the number of AAV particles generated per cell is on the order of $10^4$ particles (reviewed in Clark, 2002, Kidney Int. 61(Suppl. 1): 9-15). For a clinical study, more than $10^{15}$ particles of rAAV may be required. To produce this number of rAAV particles, transfection and culture with approximately $10^{11}$ cultured human 293 cells, the equivalent of 5,000 175-cm$^2$ flasks of cells, would be required, which means transfecting up to $10^{11}$ 293 cells. Therefore, large scale production of rAAV using mammalian cell culture systems to obtain material for clinical trials has already proven to be problematic, production at commercial scale may not even be feasible. Furthermore there is always the risk, that a vector for clinical use that is produced in a mammalian cell culture will be contaminated with undesirable, perhaps pathogenic, material present in the mammalian host cell.

To overcome these problems of mammalian productions systems, recently, an AAV production system has been developed using insect cells (Urabe et al., 2002, Hum. Gene Ther. 13: 1935-1943; US 20030148506 and US 20040197895). For production of AAV in insect cells from the baculovirus expression system some modifications were necessary because in mammalian cells expression of the three AAV capsid proteins (VP1, VP2 and VP3) in the correct stoichiometry relies on a combination of alternate usage of two splice acceptor sites and the suboptimal utilization of a ACG initiation codon for VP2 that will not be accurately reproduced by insect cells. Correct stoichiometry of the three capsid proteins is important for infectivity of the AAV particles. It is known that AAV particles containing reduced amounts of VP1 are less infectious and that VP1 contains phospholipase A2 activity which has a function in infectivity (Girod et al., 2002 J. Gen. Virol. 83: 973-8).

Therefore, for the expression of the three capsid proteins Urabe et al. (2002, supra) use a construct that is transcribed into a single polycistronic messenger that is able to express all three VP proteins without requiring splicing. To aim for production of the three capsid proteins in the correct stoichiometry, the VP1 reading frame, the first initiator codon that is seen by the scanning ribosome, has been endowed with the suboptimal initiator codon ACG and sequences surrounding this codon have been optimized. Urabe et al. (2002, supra) report that ribosome scanning through in insects cells leads to a stoichiometry of the three viral capsid proteins that is close to wild-type AAV.

The present inventors have, however, found that in AAV vectors produced in the baculovirus system VP1 is still expressed at a suboptimal level relative to VP2 and that this results in reduced infectivity in in vitro and in vivo studies in mice as compared to e.g. conventional AAV vectors produced on mammalian 293 cells. Hence, there is still a need for a baculovirus-based production system for rAAV vectors with improved infectivity.

DESCRIPTION OF THE INVENTION

Definitions

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

DETAILED DESCRIPTION OF THE INVENTION

The present invention relates the use animal parvoviruses, in particular dependoviruses such as infectious human or simian AAV, and the components thereof (e.g., an animal parvovirus genome) for use as vectors for introduction and/or expression of nucleic acids in mammalian cells. In particular, the invention relates to improvements in infectivity of such parvoviral vectors when produced in insect cells.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In a first aspect the invention relates to a nucleotide sequence comprising an open reading frame comprising nucleotide sequences encoding animal parvoviruses VP1, VP2, and VP3 capsid proteins, wherein the initiation codon for translation of the AAV VP1 capsid protein is a suboptimal initiation codon that is not ATG and that is not ACG. Suboptimal is herein understood to mean that the codon is less efficient in the initiation of translation in an otherwise identical context as compared to the normal ATG codon. Preferably the initiation codon for translation of the AAV VP1 capsid protein is selected from ACG, TTG, GTG, and CTG, more preferably the initiation codon for translation of the AAV VP1 capsid protein is selected from TTG, GTG, and CTG and most preferably the initiation codon for translation of the AAV VP1 capsid protein is CTG. The animal parvovirus preferably is a dependovirus, more preferably a human or simian adeno-associated virus (AAV).

In a nucleotide sequence comprising an open reading frame comprising nucleotide sequences encoding animal parvoviruses VP1, VP2, and VP3 capsid proteins, wherein the initiation codon for translation of the AAV VP1 capsid protein is a TTG or GTG initiation codon, the ratio of the amounts of VP1:VP2 proteins in the virion is about equal, i.e. equimolar, whereas if the initiation codon is CTG, the amount of VP1 protein in the virion is higher than the amount of VP2. If the initiation codon is ACG, the amount of VP1 protein in the virion is lower than the amount of VP2. The infectivity of the virions increases with the ratio of VP1 over VP2 in the virions.

A preferred nucleotide sequence of the invention for the expression of the AAV capsid proteins is a nucleotide sequence comprising an expression control sequence comprising a nine nucleotide sequence of SEQ. ID NO: 7 or a nucleotide sequence substantially homologous to SEQ. ID NO: 7, upstream of the initiation codon of the nucleotide sequence encoding the AAV VP1 capsid protein. A sequence with substantial identity to the nucleotide sequence of SEQ. ID NO: 7 and that will help increase expression of VP1 is e.g. a sequence which has at least 60%, 70%, 80% or 90% identity to the nine nucleotide sequence of SEQ ID NO: 7.

A further preferred nucleotide sequence of the invention for the expression of the AAV capsid proteins is a nucleotide sequence comprising an expression control sequence comprising a Kozak consensus sequence around the initiation codon of the nucleotide sequence encoding the AAV VP1 capsid protein. The Kozak consensus sequence is herein defined as GCCRCC(NNN)G (SEQ. ID NO: 8), wherein R is a purine (i.e. A or G) and wherein (NNN) stands for any of the suboptimal initiation codons as defined herein above. Preferably, in the Kozak consensus sequence in the nucleotide sequence of the invention, the R is a G. The nucleotide sequence of the invention for the expression of the AAV capsid proteins comprising a Kozak consensus sequence is thus preferably selected from GCCACC(ACG)G, GCCGCC(ACG)G, GCCACC(TTG)G, GCCGCC(TTG)G, GCCACC(GTG)G, GCCGCC(GTG)G, GCCACC(CTG)G and GCCGCC(CTG)G, more preferably the nucleotide sequence comprising the Kozak consensus sequence is selected from GCCACC(CTG)G and GCCGCC(CTG)G, most preferably, the nucleotide sequence comprising the Kozak consensus sequence is GCCGCC(CTG)G. The nucleotides in brackets herein indicate the position of the initiation codon of the VP1 protein.

The nucleotide sequence of the invention for expression of the AAV capsid proteins further preferably comprises at least one modification of the nucleotide sequence encoding AAV VP1 capsid protein selected from among a G at nucleotide position 12, an A at nucleotide position 21, and a C at nucleotide position 24. Elimination of possible false start sites for translation of VP1 of other serotypes will be well understood by an artisan of skill in the art, as will be the elimination of putative splice sites that may be recognized in insect cells. The various modifications of the wild-type AAV sequences for proper expression in insect cells is achieved by application of well-known genetic engineering techniques such as described e.g. in Sambrook and Russell (2001) "Molecular Cloning: A Laboratory Manual (3$^{rd}$ edition), Cold Spring Harbor Laboratory, Cold Spring Harbor Laboratory Press, New York. Various further modifications of VP coding regions are known to the skilled artisan which could either increase yield of VP and virion or have other desired effects, such as altered tropism or reduce antigenicity of the virion. These modifications are within the scope of the present invention.

Preferably the nucleotide sequence of the invention encoding the AAV capsid proteins is operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of the nucleotide sequence of the invention encoding of the AAV capsid proteins is e.g. the polyhedron promoter. However, other promoters that are active in insect cells are known in the art, e.g. the p10, p35 or IE-1 promoters and further promoters described in the above references.

Preferably the nucleic acid construct for expression of the AAV capsid proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

In another aspect the invention relates to an insect cell comprising a nucleic acid construct of the invention as defined above. Any insect cell which allows for replication of AAV and which can be maintained in culture can be used in accordance with the present invention. For example, the cell line used can be from Spodoptera frugiperda, drosophila cell lines, or mosquito cell lines, e.g., Aedes albopictus derived cell lines. Preferred insect cells or cell lines are cells from the insect species which are susceptible to baculovirus infection, including e.g. Se301, SeIZD2109, SeUCR1, Sf9, Sf900$^+$, Sf21, BTI-TN-5B1-4, MG-1, Tn368, HzAm1, Ha2302, Hz2E5 and High Five from Invitrogen.

A preferred insect cell according to the invention further comprises: (a) a second nucleotide sequence comprising at least one AAV inverted terminal repeat (ITR) nucleotide sequence; (b) a third nucleotide sequence comprising a Rep52 or a Rep40 coding sequence operably linked to expression control sequences for expression in an insect cell; and, (c) a fourth nucleotide sequence comprising a Rep78 or a Rep68 coding sequence operably linked to expression control sequences for expression in an insect cell.

In the context of the invention "at least one AAV ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins (e.g., Rep 78 or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An AAV replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for AAV replication of a circular vector. Thus, one ITR nucleotide sequence can be used in the context of the present invention. Preferably, however, two or another even number of regular ITRs are used. Most preferably, two ITR sequences are used. In view of the safety of viral vectors it may be desirable to construct a viral vector that is unable to further propagate after initial introduction into a cell. Such a safety mechanism for limiting undesirable vector propagation in a recipient may be provided by using rAAV with a chimeric ITR as described in US2003148506.

The number of vectors or nucleic acid constructs employed is not limiting of the invention. For example, one, two, three, four, five, six, or more vectors can be employed to produce AAV in insect cells in accordance with the present inventive method. If six vectors are employed, one vector encodes AAV VP 1, another vector encodes AAV VP2, yet another vector encodes AAV VP3, still yet another vector encodes Rep52 or Rep40, while Rep78 or Rep 68 is encoded by another vector and a final vector comprises at least one AAV ITR. Additional vectors might be employed to express, for example, Rep52 and Rep40, and Rep78 and Rep 68. If fewer than six vectors are used, the vectors can comprise various combinations of the at least one AAV ITR and the VP1, VP2, VP3, Rep52/Rep40, and Rep78/Rep68 coding sequences. Preferably, two vectors or three vectors are used, with two vectors being more preferred as described above. If two vectors are used, preferably the insect cell comprises: (a) a first nucleic acid construct for expression of the AAV capsid proteins as defined above, which construct further comprises the third and fourth nucleotide sequences as defined in (b) and (c) above, the third nucleotide sequence comprising a Rep52 or a Rep40 coding sequence operably linked to at least one expression control sequence for expression in an insect cell, and the fourth nucleotide sequence comprising a Rep78 or a Rep68 coding sequence operably linked to at least one expression control sequence for expression in an insect cell; and (b) a second nucleic acid construct comprising the second nucleotide sequence as defined in (a) above, comprising at least one AAV ITR nucleotide sequence. If three vectors are used, preferably the same configuration as used for two vectors is used except that separate vectors are used for expression of the capsid proteins and for expression of the Rep52, Rep40 Rep78 and Rep68 proteins. The sequences on each vector can be in any order relative to each other. For example, if one vector comprises ITRs and an ORF comprising nucleotide sequences encoding VP capsid proteins, the VP ORF can be located on the vector such that, upon replication of the DNA between ITR sequences, the VP ORF is replicated or not replicated. For another example, the Rep coding sequences and/or the ORF comprising nucleotide sequences encoding VP capsid proteins can be in any order on a vector. In is understood that also the second, third and further nucleic acid construct(s) preferably are an insect cell-compatible vectors, preferably a baculoviral vectors as described above. Alternatively, in the insect cell of the invention, one or more of the first nucleotide sequence, second nucleotide sequence, third nucleotide sequence, and fourth nucleotide sequence and optional further nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

The a preferred embodiment of the invention, the second nucleotide sequence present in the insect cells of the invention, i.e. the sequence comprising at least one AAV ITR, further comprises at least one nucleotide sequence encoding a gene product of interest, whereby preferably the at least one nucleotide sequence encoding a gene product of interest becomes incorporated into the genome of an AAV produced in the insect cell. Preferably, at least one nucleotide sequence encoding a gene product of interest is a sequence for expression in a mammalian cell. Preferably, the second nucleotide sequence comprises two AAV ITR nucleotide sequences and wherein the at least one nucleotide sequence encoding a gene product of interest is located between the two AAV ITR nucleotide sequences. Preferably, the nucleotide sequence encoding a gene product of interest (for expression in the mammalian cell) will be incorporated into the AAV genome produced in the insect cell if it is located between two regular ITRs, or is located on either side of an ITR engineered with two D regions.

The second nucleotide sequence defined herein above may thus comprise a nucleotide sequence encoding at least one "gene product of interest" for expression in a mammalian cell, located such that it will be incorporated into an AAV genome replicated in the insect cell. Any nucleotide sequence can be incorporated for later expression in a mammalian cell transfected with the AAV produced in accordance with the present invention. The nucleotide sequence may e.g. encode a protein it may express an RNAi agent, i.e. an RNA molecule that is capable of RNA interference such as e.g. a shRNA (short hairpinRNA) or an siRNA (short interfering RNA). "siRNA" means a small interfering RNA that is a short-length double-stranded RNA that are not toxic in mammalian cells (Elbashir et al., 2001, Nature 411: 494-98; Caplen et al., 2001, Proc. Natl. Acad. Sci. USA 98: 9742-47). In a preferred embodiment, the second nucleotide sequence may comprise two nucleotide sequences and each encodes one gene product of interest for expression in a mammalian cell. Each of the two nucleotide sequences encoding a product of interest is located such that it will be incorporated into a rAAV genome replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), and cytokines or interleukins like e.g. IL-10.

Alternatively, or in addition as a second gene product, second nucleotide sequence defined herein above may comprise a nucleotide sequence encoding a polypeptide that serve as marker proteins to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3$^{rd}$ edition), Cold Spring Harbor Laboratory, Cold Spring Harbor Laboratory Press, New York. Furthermore, second nucleotide sequence defined herein above may comprise a nucleotide sequence encoding a polypeptide that may serve as a fail-safe mechanism that allows to cure a subject from cells transduced with the rAAV of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob. Agents Chemother. 31: 844-849).

In another embodiment the gene product of interest can be an AAV protein. In particular, a Rep protein, such as Rep78 or Rep68, or a functional fragment thereof. A nucleotide sequence encoding a Rep78 and/or a Rep68, if present on the rAAV genome of the invention and expressed in a mammalian cell transduced with the rAAV of the invention, allows for integration of the rAAV into the genome of the transduced mammalian cell. Expression of Rep78 and/or Rep68 in an rAAV-transduced or infected mammalian cell can provide an advantage for certain uses of the rAAV, by allowing long term or permanent expression of any other gene product of interest introduced in the cell by the rAAV.

In the rAAV vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an α1-anti-trypsin promoter, a thyroid hormone-binding globulin promoter, an albumin promoter, LPS (thyroxine-binding globlin) promoter, HCR-ApoCII hybrid promoter, HCR-hAAT hybrid promoter and an apolipoprotein E promoter. Other examples include the E2F promoter for tumor-selective, and, in particular, neurological cell tumor-selective expression (Parr et al., 1997, Nat. Med. 3:1145-9) or the IL-2 promoter for use in mononuclear blood cells (Hagenbaugh et al., 1997, J Exp Med; 185: 2101-10).

AAV is able to infect a number of mammalian cells. See, e.g., Tratschin et al., Mol. Cell. Biol., 5(11):3251-3260 (1985) and Grimm et al., Hum. Gene Ther., 10(15):2445-2450 (1999). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al., Proc. Natl. Acad. Sci. USA, 97(7):3428-3432 (2000) (discussing differences among AAV2, AAV4, and AAV5 with respect to mammalian CNS cell tropism and transduction efficiency).

AAV sequences that may be used in the present invention for the production of AAV in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). Human or simian adeno-associated virus (AAV) serotypes are preferred sources of AAV nucleotide sequences for use in the context of the present invention, more preferably AAV serotypes which normally infects humans (e.g., serotypes 1, 2, 3A, 3B, 4, 5, and 6) or primates (e.g., serotypes 1 and 4).

Preferably the AAV ITR sequences for use in the context of the present invention are derived from AAV1, AAV2, and/or AAV4. Likewise, the Rep52, Rep40, Rep78 and/or Rep68 coding sequences are preferably derived from AAV1, AAV2, and/or AAV4. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability Rep and ITR sequences to cross-complement corresponding sequences of other serotypes allows for the production of pseudotyped AAV particles comprising the capsid proteins of a serotype (e.g., AAV3) and the Rep and/or ITR sequences of another AAV serotype (e.g., AAV2). Such pseudotyped AAV particles are a part of the present invention.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of AAV5 can differ from production of other serotypes in insect cells. Where methods of the invention are employed produce rAAV5, it is preferred that one or more vectors comprising, collectively in the case of more than one vector, a nucleotide sequence comprising an AAV5 ITR, a nucleotide sequence comprises an AAV5 Rep52 and/or Rep40 coding sequence, and a nucleotide sequence comprises an AAV5 Rep78 and/or Rep68 coding sequence. Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 in the insect cell.

In a further aspect the invention relates to an AAV virions. Preferably the AAV virion comprising in its genome at least one nucleotide sequence encoding a gene product of interest, whereby the at least one nucleotide sequence is not a native AAV nucleotide sequence, and whereby in the stoichiometry of the AAV VP1, VP2, and VP3 capsid proteins the amount of VP1: (a) is at least 100, 105, 110, 120, 150, 200 or 400% of the amount of VP2; or (b) is at least 8, 10, 10.5, 11, 12, 15, 20 or 40% of the amount of VP3; or (c) is at least as defined in both (a) and (b). Preferably, the amount of VP1, VP2 and VP3 is determined using an antibody recognizing an epitope that is common to each of VP1, VP2 and VP3. Various immunoassays are available in the art that will allow quantify the relative amounts of VP1, VP2 and/or VP3 (see e.g. Using Antibodies, E. Harlow and D. Lane, 1999, Cold Spring Harbor Laboratory Press, New York). An suitable antibody recognizing an epitope that is common to each of the three capsid proteins is e.g. the mouse anti-Cap B1 antibody (as is commercially available from Progen, Germany).

A preferred AAV according to the invention is a virion comprising in its genome at least one nucleotide sequence encoding a gene product of interest, whereby the at least one nucleotide sequence is not a native AAV nucleotide sequence, and whereby the AAV virion comprises a VP1 capsid protein that comprises a leucine or a valine at amino acid position 1. A more preferred AAV virion according to the invention has the ratio's of capsid proteins as defined above and comprises a VP1 capsid protein comprises a leucine or a valine at amino acid position 1. Even more preferred is an AAV virion that is obtainable from an insect cell as defined above in e.g. a method as defined herein below.

An advantage of the AAV virions of the invention that have the above defined ratio's of capsid proteins is their improved infectivity. In particular the infectivity increases with an increase of the amount of VP1 protein in the capsid in relation to the amounts of VP2 and/or VP3 in the capsid. The infectivity of an AAV virion is herein understood to mean the efficiency of transduction of the transgene comprised in the virion, as may be deduced from the expression rate of the transgene and the amount or activity of the product expressed from the transgene.

In another aspect the invention thus relates to a method for producing an AAV in an insect cell. Preferably the method comprises the steps of: (a) culturing an insect cell as defined in herein above under conditions such that AAV is produced; and, (b) recovery of the AAV. Growing conditions for insect cells in culture, and production of heterologous products in insect cells in culture are well-known in the art and described e.g. in the above cited references on molecular engineering of insects cells.

Preferably the method further comprises the step of affinity-purification of the AAV using an anti-AAV antibody, preferably an immobilized antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of AAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

DESCRIPTION OF THE FIGURES

FIG. 5 FIG. 1: Four AAV1-batches produced in insect cells with the baculovirus expression system were loaded onto a Nupage gel to evaluate the VP1,2,3 stoichiometry. Lanes: AAV1-batch prepared with a baculovirus-Cap construct containing VP1-initiation codon CTG (lane 1), GTG (lane 2), ACG (lane 3), TTG (lane4). As a control a plasmid-produced AAV1-batch (FSB-02) was loaded (lane5). The stoichiometry of AAV1 using a CTG-initiation codon is comparable with the FSB-02 batch.

EXAMPLES

Figure 1:
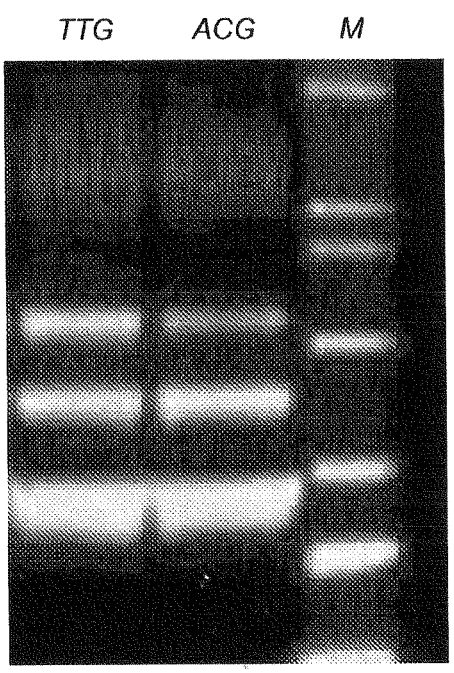
FIG. 1: Western-blot analysis of rAAV produced with a recombinant baculovirus containing a TTG or an ACG initiation codon for the VP1 capsid protein.

1. Materials & Methods
1.1 Baculovirus Plasmid Construction

In order to express VP1,2,3 from a sole polycistronic messenger RNA, the baculovirus-AAV-Cap construct was designed as described by (Urabe et al., 2002, supra). Briefly, the ATG initiation codon of VP1 was mutated to ACG. A potential ATG initiation codon at position 11 has been changed to ACG. The splice acceptor site downstream of the VP1 initiation codon was destroyed (mutation at position 21 and 24). The mutated Cap expression cassette was cloned into a baculovirus expression construct; pFastBacDual (pFBDAAV1VPm11) with BamH1/StuI restriction sites. This plasmid (pFBDAAV1VPm11) was the starting material for introduction of alternate initiation codons for VP1. The forward primer used by Urabe et al. (2002, supra) in order to introduce the mentioned mutations was:

```
                                        (SEQ ID NO. 1)
   BamHI       1        11       21 24
5'-cgcggatcctgttaagACGGCTGCCGACGGTTATCTACCCGATT
GGCTC-3'
```

The following forward primers were used to make the expression constructs using pFBDAAV1VPm11 (Urabe et al., 2002, supra) as starting material:

```
                                        (SEQ ID NO. 2)
5'-cgcggatcctgttaagTTGGCTGCCGACGGTTATCTACCCGATT
GGCTC-3'

(SEQ ID NO. 3)
5'-cgcggatcctgttaagATTGCTGCCGACGGTTATCTACCCGATT
GGCTC-3'

(SEQ ID NO. 4)
5'-cgcggatcctgttaagGTGGCTGCCGACGGTTATCTACCCGATT
GGCTC-3'

(SEQ ID NO. 5)
5'-cgcggatcctgttaagCTGGCTGCCGACGGTTATCTACCCGATT
GGCTC-3'
```

In addition, two forward primers were used to prepare constructs wherein the ACG and CTG codons, respectively are preceded with a preferred form of the Kozak sequence "GCCGCC(NNN)G" (see SEQ ID NO: 8; and wherein (NNN) stands for the suboptimal initiation codon).

```
                                        (SEQ ID NO. 9)
5'-ccatcgggcgcggatcctgqccgccACGGCTGCCGACGGTTATC
TAC-3'

(SEQ ID NO. 10)
5'-ccatcgggcgcggatcctqccaccCTGGCTGCCGACGGTTATCT
AC-3'
```

The backward-primer that was used in the PCR reactions with the above forward primers was directed to position ~230 bp downstream of the VP1 initiation codon and contains a unique Stu I site (AGGCCT).

```
                                        (SEQ ID NO. 6)
        5'-GTCGTAGGCCTTGTCGTGCTCGAGGGCCGC-3'
```

Fragments were amplified with the above-mentioned sets of forward and backward primer pairs by PCR. Following digestion of PCR products with BamHI and StuI the PCR products were subcloned into the BamHI/StuI sites of pFBDAAV1vpm11 resulting in the various to be tested baculovirus-AAV-Cap constructs. DNA constructs were verified by sequence analysis at Baseclear, Leiden, the Netherlands.

1.2 Recombinant Baculovirus Production

Recombinant baculoviruses derived from the *Autographa californica* nuclear polyhydrosis virus (AcNPV) were produced using the Bac-to-Bac baculovirus expression system (Invitrogen). rBac-Cap was amplified by infecting $2\times10^6$ Sf9 cells per ml at an moi of 0.1. Three days after infection the cells were spun down and the supernatant containing the virus recovered.

rAAV batches were produced using three recombinant baculoviruses according to Urabe et al., 2002. However, for this study one baculovirus harbored an expression construct for the $LPL^{S447X}$-transgene. The therapeutically active agent expressed from the transgene is a naturally occurring variant of human lipoprotein lipase, a single chain polypeptide of 448 amino acids. The $LPL^{S447X}$ variant has a deletion of two amino acids at the C-terminus of the protein. The second baculovirus harboured an expression construct for the AAV replication genes, Rep 78 and Rep 52. The third baculovirus harboured the AAV1 capsid sequence with either an ACG or a TTG, CTG, GTG initiation codon for VP1.

Mammalian-rAAV batches produced with the plasmid-transfection system were produced according to Grimm et al., 1998 (Novel tools for production and purification of recombinant adeno-associated virus vectors. Hum Gene Ther. 1998 Dec. 10; 9(18):2745-60).

1.3 Western Blot Analysis

Insect cells were infected with baculovirus-Cap. At three days post-infection cells were centrifuged (3,000 g; 15 min). The supernatant was filtered through a 0.22 um Millex filter. NuPAGE LDS sample buffer (Invitrogen) was added to a sample of the supernatant and was loaded onto a 4-12% Bis-Tris gel. The gel was run at 100V. Proteins were blotted onto a nitrocellulose membrane (BioRad) for 1 hr, 100V, 350 mA. Western immunochemistry was performed by blocking the membrane with 1% marvel, dried skimmed milk and subsequently incubation with mouse anti-Cap (B1 from Progen, Germany; dilution 1:50) and rabbit anti-mouse-HRP (DAKO, dilution 1:100). VP1, 2 and 3 were visualized by chemoluminescent staining with lumi-light plus Western-blotting substrate (Roche).

1.4 Biochemical Measurements

Human $LPL^{S447X}$ activity was assayed as previously described using a radioactive trioleoylglycerol emulsion substrate (Nilsson-Ehle and Scholtz, 1976). Human $LPL^{S447X}$ immunoreactive mass was assayed using a sandwich ELISA with chicken IgY and mouse 5D2 anti-hLPL antibodies (Liu et al., 2000). Plasma triglyceride levels were measured by using commercial kits following manufacturer protocols (Boehringer Mannheim, #450032).

2. Results
2.1 Construction of Recombinant Baculovirus

In order to introduce different alternate initiation codons for VP1 expression in the baculovirus plasmid designed by Urabe et al. (2002, supra) a series of upstream primers were designed containing a BamHI restriction site and either a TTG, ATT, GTG or CTG codon in place of the ACG initiation codon of VP1. PCR using these primers in combination with a downstream primer containing a StuI site resulted in amplified fragments that were subcloned into the BamHI/StuI site of pFBDVPm11 (Bac-Cap). The resulting baculovirus plasmids were used for the preparation of recombinant baculoviruses using the Bac-to-Bac baculovirus expression system. The prepared recombinant baculoviruses were infected on insect cells in order to produce AAV capsids. At three days following infection viral protein expression of the different baculovirus batches were determined on Western blots. From the Western blots it became clear that the baculovirus construct containing the TTG initiation codon for VP1 expressed this protein to a higher level compared to the previously used ACG initiation codon. The ratio between VP1 and VP2 using the TTG codon was found to be 1:1 which is similar to what is reported for wild type AAV (FIG. 1).

2.2 Infection of rAAV Batches on Cells in Culture

Figure 2:
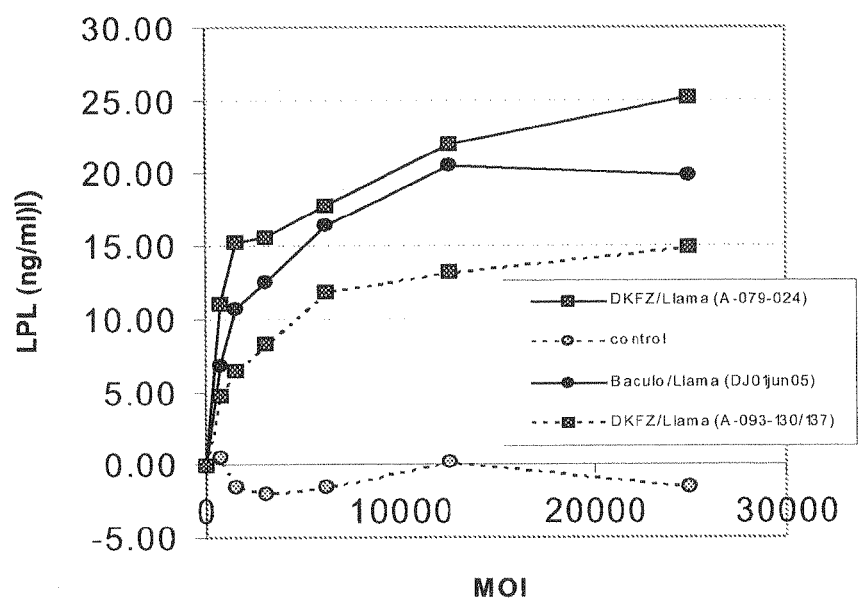
FIG. 2: LPL-mass assay: HEK293 cells in a microtiter plate were infected with rAAV produced with the baculovirus-production system and the plasmid-production system at and moi between 100 and 25,000. At two days after infection $LPL^{S447X}$ protein was measured by $LPL^{S447X}$-mass ELISA. "DKFZ/Llama" (A-079-024 and A-093-130/137) represent rAAV-$LPL^{S447X}$ batches generated with the plasmid production system. "Control" represents a rAAV-LacZ virus batch not expressing $LPL^{S447X}$ but the bacterial protein LacZ. Baculo/Llama represents a rAAV-$LPL^{S447X}$ batch generated with the baculovirus production system using the rBac-Cap virus with the TTG-initiation codon.

In order to investigate the infectivity of the AAV capsids derived from recombinant baculoviruses with the TTG initiation codon rAAV was generated. Also a rAAV batch was generated by plasmid transfection on mammalian HEK293 cells. A vector genome titer of both rAAV batches was determined by qPCR. This titer was used to infect HEK 293 cells in a microtiter plate at an increasing moi. At two days following infection an quantitative assay ($LPL^{S447X}$-mass assay) for the transgene product ($LPL^{S447X}$) was performed on the medium of the infected cells. The assay showed that the amount of $LPL^{S447X}$ produced by baculovirus-produced rAAV was similar to the LPL produced by the plasmid-produced rAAV (FIG. 2).

2.3 Injection of rAAV Batches in Mice

Figure 3:
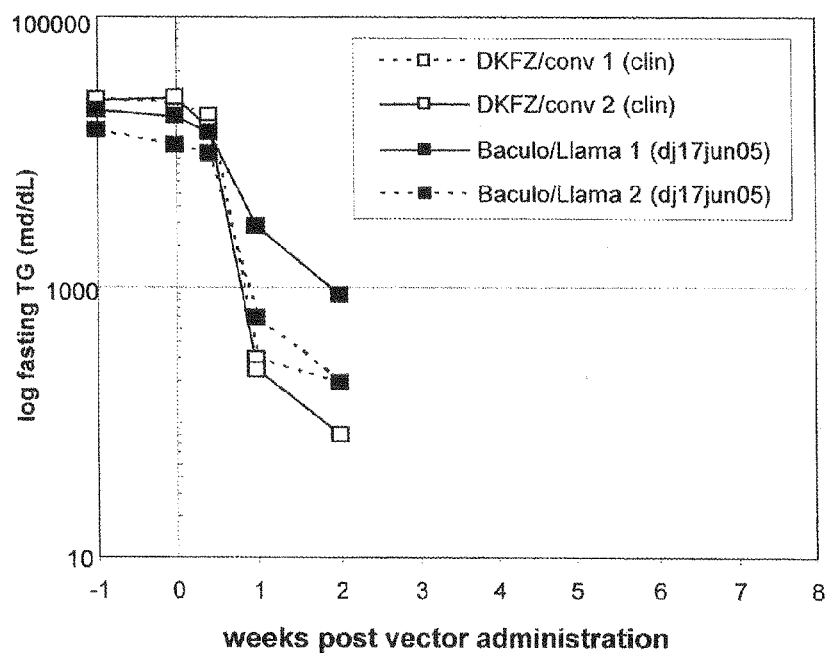
FIG. 3: Tryglycerides (TG) level in blood plasma was determined following injection of AAV vector batches. Mice (n=2) were injected with rAAV produced with the baculovirus-production system (DJ17jun05) and (n=2) the mammalian-production system (Clin). At 3, 7 and 14 days post-administration of the vector blood samples were taken and assayed for TG fasting.
Figure 3:
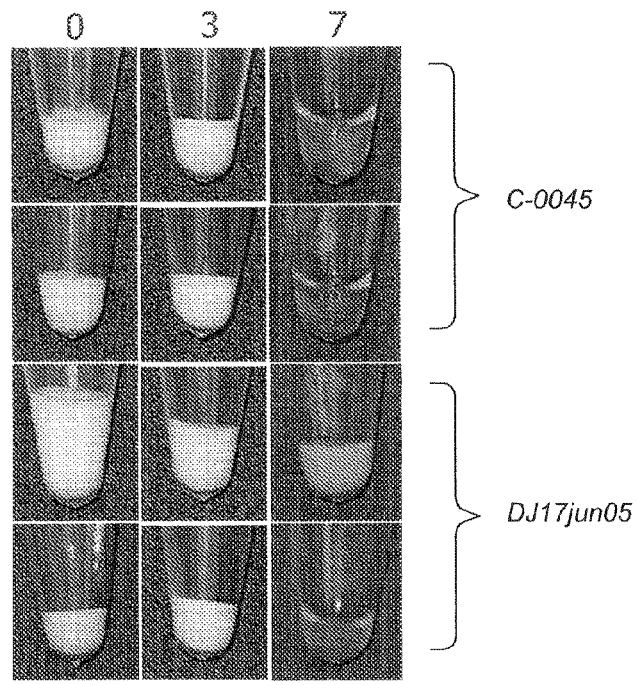
Figure 4:
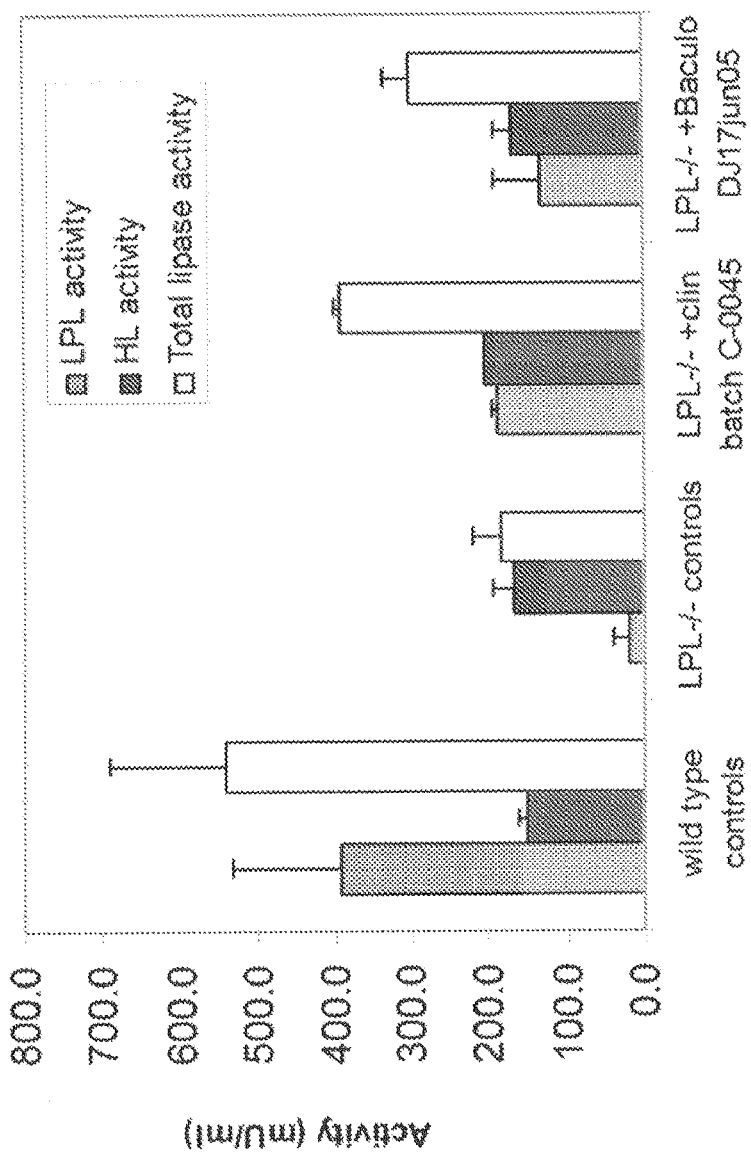
FIG. 4: $LPL^{S447X}$-activity was measured in plasma samples: mice were injected with rAAV produced with the baculovirus-production system (DJ17jun05) and the mammalian-production system (C-0045). At 14 days post-administration of the vector blood samples were taken and $LPL^{S447X}$-activity was determined.

The rAAV batches produced with the baculovirus-production system and with the conventional mammalian plasmid-production system were injected intramuscularly in mice to follow $LPL^{S447X}$-protein activity and triglyceride fasting in vivo. At 3 days, 7 days and at 2 weeks following injection blood samples were taken and evaluated. Between 3 and 7 days post virus administration blood-plasma sampled from both mice injected with mammalian-rAAV and one mouse injected with baculo-rAAV was turned from milky to completely clear. Blood plasma derived from one baculo-rAAV-injected mouse remained relatively milky however fat level was clearly reduced. Triglyceride levels were lowered respectively of all treated mice (FIG. 3). On day 14 TG levels in both mammalian-AAV and baculovirus-(TTG)-AAV treated mice TG levels were reduced for 96%. Plasma samples taken at two weeks after virus administration showed that the $LPL^{S447X}$-activity of the mice treated with baculovirus-AAV and mammalian-AAV was similar (FIG. 4).

2.4 Production of Recombinant AAV Batches with Different Vp1-Initiation Codons

Figure 5:
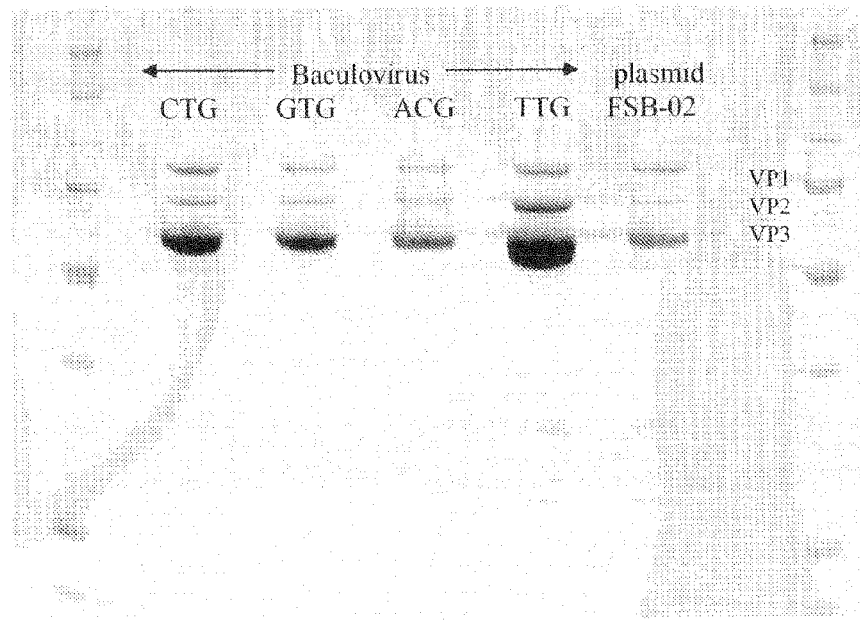

Recombinant baculoviruses containing a AAV-Cap type 1 expression unit with different VP1-initiation codons (CTG, GTG, TTG, ACG) were used to prepare rAAV1-LPL batches in insect cells. The viruses batches were purified and loaded onto a NuPage gel for evaluation (FIG. 5). The gel shows the stoichiometry between the VP1, VP2 and VP3 proteins of the various viruses. First we point to the previously produced rAAV1-LPL using a conventional plasmid-transfection system (pPD1, DKFZ, Heidelberg, Germany) on HEK293 cells. In our hands this system produces an unusual stoichiometry between the VP1, VP2 and VP3 proteins whereby VP1 is present in a higher amount than VP2. This stoichiometry is significantly different from the 1:1:10 reported stoichiometry for the VP1, VP2 and VP3 proteins as is seen in wtAAV or other mammalian AAV vector production platforms.

In the Baculovirus system, the rAAV construct with the CTG codon produces virus that has a significantly higher amount of VP1 compared to the amount of VP2 in the capsid. In this particular experiment (FIG. 5) the stoichiometry of the VP1, VP2 and VP3 capsid proteins produced with BAC-Cap GTG or ACG constructs show similar VP1 to VP2-ratio's on gel and the TTG construct appears to express slightly less VP1 than VP2. However, we have repeatedly found that TTG and GTG constructs show a similar stoichiometry whereby the VP1 and VP2 proteins are present in about equal amounts, whereas the ACG construct usually produces a stoichiometry whereby there is less VP1 than VP2 protein. The CTG constructs consistently produce a stoichiometry whereby there is more VP1 than VP2 protein.

To further improve production rates of rAAV we prepared constructs wherein the ACG and CTG codons, respectively are present in a Kozak consensus sequence "GCCGCC (NNN)G" (see SEQ. ID NO: 8), wherein "(NNN)" identifies the position of the ACG and CTG codons, respectively. AAV production in insect cells from the construct wherein the CTG codon is preceded with the Kozak sequence resulted in significantly higher AAV production than the construct without the Kozak sequence (data not shown). In contrast, AAV production in insect cells from the construct wherein an ACG codon is preceded with the Kozak sequence did not result in higher AAV production (data not shown).

2.5 Injection of rAAV Batches in Mice

Figure 6:
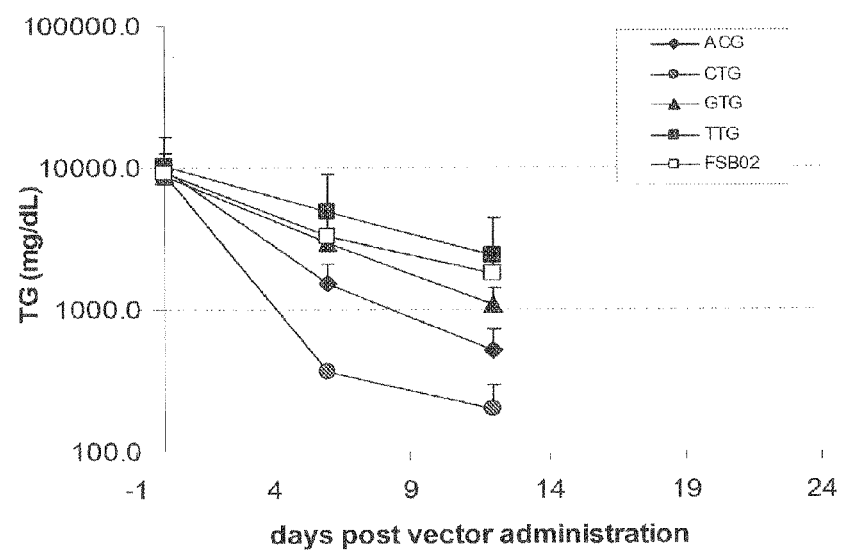
FIG. 6 Batches of AAV1-LPL were injected in muscle of LPL-deficient (−/−) mice with $3 \times 10^{12}$ gc/kg. The AAV1-LPL batch prepared with the rBac-Cap construct containing the CTG-initiation codon performs significantly better in terms of Triglyceride (TG) lowering compared to the other batches.

In order to verify that the content of VP1 in the viral capsid is linked to vector infectivity the baculovirus-produced AAV1 batches and the plasmid-produced AAV1 batch were injected in the muscle of homozygous LPL (−/−) mice and Triglyceride (TG) lowering as a result of active LPL-expression was monitored in time (FIG. 6). The results show that the AAV1-LPL batch produced with the CTG-initiation codon as expected lowers TG-levels faster and more profound compared to the other AAV1 batches. Remarkable however is that, although stoichiometry is similar, the TG-lowering with the baculo-CTG mutant is even more profound compared to the plasmid-produced AAV1 (produced with pDP1).

We have repeatedly seen that baculovirus-produced AAV made with the CTG construct performed better, i.e. showed a higher infectivity, both in vitro and in vivo compared to AAV made with the other suboptimal initiation codon constructs, especially when compared with the construct with the ACG codon. We have also repeatedly seen that the VP1 content in AAV virions made with the CTG construct contains more VP1 compared to VP2 and that this is not the case with the other constructs, especially ACG.

The invention claimed is:

1. A nucleic acid construct comprising a nucleotide sequence encoding adeno-associated virus (AAV) VP1, VP2, and VP3 capsid proteins, wherein the initiation codon for translation of the AAV VP1 capsid protein is CTG, TTG, or GTG and wherein the nucleotide sequence is operably linked to an expression control sequence for expression in an insect cell.

2. A nucleic acid construct according to claim 1, wherein the initiation codon is CTG.

3. A nucleic acid construct according to claim 1, wherein the expression control sequence comprises a nine nucleotide sequence of SEQ ID NO:7 or a sequence substantially homologous to SEQ ID NO:7 upstream of the initiation codon.

4. A nucleic acid construct according to claim 1, wherein the expression control sequence comprises a Kozak consensus sequence around the initiation codon, which Kozak consensus sequence is GCCRCCNNNG (SEQ ID NO:8), wherein R is a purine and wherein NNN is the initiation codon.

5. A nucleic acid construct according to claim 1, wherein the nucleotide sequence encoding said AAV VP1 capsid protein comprises at least one modification selected from the group consisting of G at position 12, an A at position 21, and a C at position 24.

6. A nucleic acid construct according to claim 1, wherein the nucleotide sequence is operably linked to a polyhedron promoter.

7. A nucleic acid construct according to claim 1 that is in the form of a baculoviral vector capable of productive transformation or transfection of an insect cell.

8. An insect cell comprising the nucleic acid construct according to claim 1.

9. An insect cell according to claim 8, that further comprises:
   (a) a second nucleotide sequence comprising at least one AAV inverted terminal repeat (ITR) nucleotide sequence;
   (b) a third nucleotide sequence comprising a Rep52 or a Rep40 coding sequence operably linked to expression control sequences for expression in an insect cell; and,
   (c) a fourth nucleotide sequence comprising a Rep78 or a Rep68 coding sequence operably linked to expression control sequences for expression in an insect cell.

10. An insect cell according to claim 9, that comprises:
   (a) a first nucleic acid construct comprising,
      (i) a first nucleotide sequence encoding AAV VP1, VP2, and VP3 capsid proteins, wherein the initiation codon for translation of the VP1 capsid protein is CTG, TTG, or GTG and wherein the nucleotide sequence is operably linked to an expression control sequence for expression in an insect cell;
      (ii) the third nucleotide sequence as defined in claim 9(b); and
      (iii) the fourth nucleotide sequence as defined in claim 9(c); and,
   (b) a second nucleic acid construct comprising the second nucleotide sequence as defined in claim 9(a).

11. An insect cell according to claim 10, wherein the first and/or second nucleic acid construct is in the form of a baculoviral vector capable of productive transformation or transfection of an insect cell.

12. An insect cell according to claim 9, wherein the second nucleotide sequence further comprises at least one nucleotide sequence encoding a gene product of interest for expression in a mammalian cell, which coding sequence becomes incorporated into the genome of an AAV produced in the insect cell.

13. An insect cell according to claim 12, wherein the second nucleotide sequence comprises two AAV ITR nucleotide sequences between which is located the at least one sequence encoding the product of interest.

14. The insect cell according to claim 9, wherein the first nucleotide sequence, the second nucleotide sequence, the third nucleotide sequence, and the fourth nucleotide sequence are stably integrated in the genome of the insect cell.

15. An AAV virion comprising in its genome at least one nucleotide sequence encoding a gene product of interest, which sequence is not a native AAV nucleotide sequence, and wherein VP1 capsid protein is present in the virion in at least 110% of the amount of capsid protein VP2 and at least 11% of the amount of capsid protein VP3, the amount of said capsid proteins being determined using an antibody that recognizes an epitope that is common to each of VP1, VP2 and VP3.

16. An AAV virion comprising in its genome at least one nucleotide sequence encoding a gene product of interest which sequence is not a native AAV nucleotide sequence, and wherein the virion comprises a VP1 capsid protein comprising leucine or valine at amino acid position 1.

17. An AAV virion according to claim 15, wherein the VP1 capsid protein comprises leucine or valine at amino acid position 1.

18. A method for producing an AAV virion in an insect cell, comprising the steps of:
(a) culturing the insect cell according to claim 8 under conditions such that the AAV virion is produced; and,
(b) recovering the AAV virion.

19. A method according to claim 18, further comprising the step of affinity-purifying the AAV virion using an anti-AAV antibody.

20. A method according to claim 19, wherein the anti-AAV antibody is a single chain cameloid antibody or a fragment thereof.

21. The method according to claim 19, wherein the antibody is immobilized.

* * * * *